(12) United States Patent
Jung

(10) Patent No.: US 8,862,380 B2
(45) Date of Patent: Oct. 14, 2014

(54) SYSTEM AND METHOD FOR ALARMING FRONT IMPACT DANGER COUPLED WITH DRIVER VIEWING DIRECTION AND VEHICLE USING THE SAME

(75) Inventor: Ho Choul Jung, Suwon (KR)

(73) Assignee: Hyundai Motor Company, Seoul (KR)

( * ) Notice: Subject to any disclaimer, the term of this patent is extended or adjusted under 35 U.S.C. 154(b) by 853 days.

(21) Appl. No.: 12/952,090

(22) Filed: Nov. 22, 2010

(65) Prior Publication Data

US 2012/0089321 A1 Apr. 12, 2012

(30) Foreign Application Priority Data

Oct. 11, 2010 (KR) ........................ 10-2010-0098894

(51) Int. Cl.
| | | |
|---|---|---|
| *G06F 19/00* | (2011.01) | |
| *B60Q 1/00* | (2006.01) | |
| *G06T 7/00* | (2006.01) | |
| *G01C 21/36* | (2006.01) | |
| *B60K 28/06* | (2006.01) | |
| *A61B 3/113* | (2006.01) | |
| *G08G 1/16* | (2006.01) | |
| *B60W 30/095* | (2012.01) | |
| *B60W 50/14* | (2012.01) | |
| *B60W 30/09* | (2012.01) | |
| *G06K 9/00* | (2006.01) | |
| *B60W 30/085* | (2012.01) | |

(52) U.S. Cl.
CPC .............. *G08G 1/166* (2013.01); *G06T 7/0046* (2013.01); *B60W 2550/14* (2013.01); *B60W 2050/143* (2013.01); *B60W 2550/22* (2013.01); *G01C 21/3602* (2013.01); *B60K 28/066* (2013.01); *A61B 3/113* (2013.01); *B60W 50/14* (2013.01); *G01C 21/3697* (2013.01); *G06T 2207/30201* (2013.01); *B60W 2550/402* (2013.01); *B60W 30/09* (2013.01); *G06K 9/00248* (2013.01); *B60W 2540/30* (2013.01); *B60Y 2300/18158* (2013.01); *B60W 30/095* (2013.01); *G06K 9/00604* (2013.01); *G06K 9/00845* (2013.01); *B60W 30/085* (2013.01)

USPC ............ 701/301; 701/300; 340/435; 340/903

(58) Field of Classification Search
CPC ........... A61B 3/113; B60W 2050/143; B60W 30/09; B60W 30/085; B60W 30/095; B60W 50/14; B60W 2550/14; B60W 2550/22; B60W 2550/402; G01C 21/3602; G01C 21/3697; G01J 3/0289; G06K 9/00248; G06K 9/00604; G06K 9/00845; G06T 2207/30201; G06T 7/0046; G08G 1/166; B60K 28/066; B60Y 2300/18158

USPC .......................... 701/301, 300; 340/903, 435

See application file for complete search history.

(56) References Cited

U.S. PATENT DOCUMENTS 5,450,057 A * 9/1995 Watanabe ..................... 340/435
5,732,385 A * 3/1998 Nakayama et al. ........... 701/437

(Continued)

FOREIGN PATENT DOCUMENTS

| JP | 05-290299 A | 11/1993 |
|---|---|---|
| JP | 11-139229 A | 5/1999 |

(Continued)

*Primary Examiner* — Calvin Cheung
*Assistant Examiner* — Angelina Shudy
(74) *Attorney, Agent, or Firm* — Edwards Wildman Palmer LLP; Peter F. Corless

(57) ABSTRACT

Featured are a system and a method for alarming a front impact danger coupled with a driver viewing direction and a vehicle Such a system includes: a driver viewing direction recognition unit recognizing a driver viewing direction; an obstacle sensing unit sensing obstacles existing in directions that a driver does not view; and an engine control unit. The engine control unit receives and analyzes the driver face direction data from the driver viewing direction recognition unit to identify the driver viewing direction when the vehicle enters in the crossroads, requests the obstacle sensing unit perform obstacle sensing for another direction than the driver's viewing direction and analyzes analyze an obstacle sensing result. Such methods advantageously warns a driver to the presence of obstacles when a vehicle enters in crossroads to prevent a traffic accident.

17 Claims, 7 Drawing Sheets

(56) References Cited

U.S. PATENT DOCUMENTS

| | | | |
|---|---|---|---|
| 5,940,010 A * | 8/1999 | Sasaki et al. | 340/901 |
| 6,072,391 A * | 6/2000 | Suzuki et al. | 340/468 |
| 6,370,475 B1 * | 4/2002 | Breed et al. | 701/301 |
| 6,516,273 B1 * | 2/2003 | Pierowicz et al. | 701/301 |
| 6,606,027 B1 * | 8/2003 | Reeves et al. | 340/436 |
| 6,617,981 B2 * | 9/2003 | Basinger | 340/909 |
| 6,882,303 B2 * | 4/2005 | Samukawa et al. | 342/70 |
| 7,039,521 B2 * | 5/2006 | Hortner et al. | 701/436 |
| 7,347,479 B2 * | 3/2008 | Suzuki et al. | 296/97.1 |
| 7,692,550 B2 * | 4/2010 | Bonefas et al. | 340/575 |
| 7,692,551 B2 * | 4/2010 | Bonefas et al. | 340/575 |
| 8,004,599 B2 * | 8/2011 | Misawa | 348/349 |
| 8,068,036 B2 * | 11/2011 | Ghazarian | 340/903 |
| 8,179,241 B2 * | 5/2012 | Sakai et al. | 340/436 |
| 8,362,922 B2 * | 1/2013 | Kushi et al. | 340/905 |
| 8,395,530 B2 * | 3/2013 | Al-Hasan | 340/907 |
| 8,576,065 B2 * | 11/2013 | Buck et al. | 340/539.13 |
| 2004/0239509 A1 * | 12/2004 | Kisacanin et al. | 340/575 |
| 2005/0251313 A1 * | 11/2005 | Heinrichs-Bartscher | 701/41 |
| 2005/0264021 A1 * | 12/2005 | Suzuki et al. | 296/97.4 |
| 2006/0195241 A1 * | 8/2006 | Nakagoshi | 701/45 |
| 2007/0154095 A1 * | 7/2007 | Cao et al. | 382/190 |
| 2007/0162922 A1 * | 7/2007 | Park | 725/10 |
| 2007/0247524 A1 * | 10/2007 | Yoshinaga et al. | 348/78 |
| 2008/0300010 A1 * | 12/2008 | Border et al. | 455/556.1 |
| 2009/0012709 A1 * | 1/2009 | Miyazaki | 701/223 |
| 2009/0128311 A1 * | 5/2009 | Nishimura et al. | 340/435 |
| 2009/0140881 A1 * | 6/2009 | Sakai et al. | 340/901 |
| 2009/0220156 A1 * | 9/2009 | Ito et al. | 382/201 |
| 2009/0226095 A1 * | 9/2009 | Usui | 382/195 |
| 2009/0243880 A1 * | 10/2009 | Kiuchi | 340/903 |
| 2009/0284799 A1 * | 11/2009 | Matsuhira | 358/3.24 |
| 2011/0313665 A1 * | 12/2011 | Lueke et al. | 701/301 |
| 2012/0002027 A1 * | 1/2012 | Takahashi et al. | 348/77 |
| 2012/0169596 A1 * | 7/2012 | Zhuang | 345/158 |
| 2013/0184979 A1 * | 7/2013 | Karandikar | 701/301 |

FOREIGN PATENT DOCUMENTS

| | | |
|---|---|---|
| JP | 2002-367100 A | 12/2002 |
| JP | 2005-081101 A | 3/2005 |
| JP | 2005-153660 A | 6/2005 |
| JP | 2006-163828 A | 6/2006 |
| JP | 2007-072629 A | 3/2007 |
| JP | 2007-249757 A | 9/2007 |
| JP | 2008-097278 A | 4/2008 |
| KR | 20-1998-0011972 U | 5/1998 |
| KR | 1020070045395 A | 5/2007 |
| KR | 100892518 B1 | 4/2009 |
| KR | 10-2009-0104607 A | 10/2009 |

* cited by examiner

SYSTEM AND METHOD FOR ALARMING FRONT IMPACT DANGER COUPLED WITH DRIVER VIEWING DIRECTION AND VEHICLE USING THE SAME

CROSS-REFERENCES TO RELATED APPLICATIONS

Priority is claimed to Korean patent application number 10-2010-0098894, filed on Oct. 11, 2010, which is incorporated by reference in its entirety.

BACKGROUND OF THE INVENTION

1. Field of the Invention

The present invention relates to a system and a method for providing an alarm of a front impact danger as well as a vehicle using such a system. The present invention more particularly relates to systems, methods and vehicles embodying same in which road specific information, driver viewing direction and sensing of obstacles in a moving direction of a car while a driver is viewing in another direction is used to provide such an alarm of a potential impact.

2. Description of the Related Art

In recent years, as social and economic scales are enlarged and become high level, vehicles and traffic demands are significantly increased so as to create potential for serious traffic problem in a large city. In particular, when many vehicles and walkers sequentially enter in intersections or crossroads, the driver of the vehicle checks to determine if obstacles exist in a moving direction of a vehicle while also checking to see if a vehicle is coming from a direction different from the moving direction of the vehicle, to determine if the driver should slowly enter in the crossroads.

However, it is difficult for the driver to simultaneously check the moving direction (left) of the vehicle and another or opposite direction (right), by turning their head. Although a driver can approximately check out the moving direction of the vehicle and the opposite direction thereto, if the driver does not identify rapidly entered obstacles (vehicles or walkers of signal violation), a traffic accident can occur that can lead to human and physical disaster. For example, even if a driver has checked both ways at an intersection or cross roads, a pedestrian or jogger can walk or jog in front of the vehicle assuming that the vehicle is stopped.

It thus would be desirable to provide systems and methods that can provide an alarm of a front impact danger as well as a vehicle using such a system. It would be particularly desirable to provide such system and methods which can use road specific information, driver viewing direction and sensing of obstacles in a moving direction of a car while a driver is viewing in another direction so as to provide such an alarm of a potential impact.

SUMMARY OF THE INVENTION

The present invention features a system and a method for that provides an alarm of a front impact danger, coupled with a driver viewing direction and sensing of obstacles in a first direction that is opposite to a driver viewing direction, a second direction. The first direction is a direction that the driver cannot view. Such systems and methods advantageously allows a driver to safely enter and intersection or crossroads. In further embodiments, such systems and methods are performed in conjunction with a navigation unit.

In accordance with an aspect of the present invention, there is featured a system for alarming a front impact danger coupled with a driver viewing direction. Such a system includes: a driver viewing direction recognition unit that recognizes a driver's viewing direction; an obstacle sensing unit that senses obstacles existing in directions that a driver does not view (i.e., the first direction); and an engine control unit. Such a engine control unit is configured so as to receive and analyze driver face direction data that is transmitted by the driver viewing direction recognition unit, to identify the driver viewing direction when the vehicle enters the intersection or crossroads. Such an engine control unit also outputs a signal or command to the obstacle sensing unit, requesting obstacle sensing for a direction opposite to the driver viewing direction. The output of the obstacle sensing unit (an obstacle sensing result) is analyzed by the engine control unit.

In embodiments of the present invention, such a system for alarming further includes a navigation unit that provides information regarding the intersection or crossroads and moving direction information of the vehicle to the engine control unit.

In further embodiments, such a system for alarming further includes an alarm sound output unit that outputs an alarm sound or auditory signal responsive to a control signal from the engine control unit.

In yet further embodiments, the engine control unit checks whether both eyes are detected in the face direction data, calculates a both eyes based face direction angle when the both eyes are detected, and calculates a face direction angle when the both eyes are detected or when one eye is detected.

In yet more particular embodiments, the engine control unit makes a triangle based on a center of a left eye, a center of a right eye, and a nose center from the face direction data; and connects the nose center to a center point of the left eye center and the right eye center; connects a point drawing, a perpendicular line perpendicular to a line that connects the left eye center and the right eye center from the center point of the left eye center and the right eye center to the nose center (N) to form a triangle, more specifically a right triangle. The engine control unit thus calculates an angle toward center point of the left eye center and the right eye center as the both eyes based face direction angle.

The engine control unit calculates the face direction angle using a distance between a right end of a driver face and a left end of the driver face, a distance between the right end of the driver face and a nose center, and a distance between the left end of the driver face and the nose center in the face direction data.

The engine control unit also calculates the face direction angle using a distance between a right end of a driver face and a left end of the driver face, a distance between the right end of a driver face and a nose center, and a distance between the left end of a driver face and the nose center in the face direction data and stores the calculated face direction angle in a look-up table. The engine control unit determines a driver viewing direction, using the look-up table, when receiving the face data from the driver viewing direction recognition unit. The driver viewing direction recognition unit is an imaging device such as for example a camera (e.g., a CCD type of camera). The obstacle sensing unit is one of a number of sensing devices as is known to those skilled in the art including but not limited to a device or sensor embodying radar, an imaging device such as a camera, a device or sensor embodying a laser, or an ultrasonic sensor. In further embodiments, a direction of the obstacle sensing unit is changeable such as for, example, by a motor (e.g., indexing electric motor) that is operably coupled to the sensing unit and coupled with the driver viewing direction.

In accordance with another aspect of the present invention, there is featured a method for alarming a front impact danger coupled with a driver viewing direction. Such a method includes: receiving road specific information such as crossroads information or intersection information and receiving moving direction information of a vehicle when the vehicle enters a crossroads or intersection. Such a method also includes checking the driver viewing direction and sensing obstacles existing in another direction that the driver does not view. In addition, such a method includes checking whether the driver enters in the moving direction of the vehicle according to presence of the obstacle as the sensing result of the obstacle.

In further embodiments, such checking the driver viewing direction includes: imaging or photographing the driver's face; checking whether both eyes are detected from the image data of the driver's face (or data photographing the driver's face); calculating a both eyes based face direction angle when the both eyes are detected; and calculating a face contour based face direction angle when the both eyes are not detected or one of the both eyes is detected.

In further embodiments, such calculating a both eyes based face direction angle includes making a triangle based on a center of a left eye, a center of a right eye, and a nose center from the face direction data, connecting the nose center to a center point of the left eye center and the right eye center, connecting a point drawing, a perpendicular line perpendicular to a line that connects the left eye center and the right eye center from the center point of the left eye center and the right eye center to the nose center (N) to form a triangle (e.g., an right triangle) to thereby calculate an angle toward center point of the left eye center and the right eye center as the both eyes based face direction angle.

Such calculating a face direction angle includes calculating the face direction angle using a distance between a right end of a driver face and a left end of the driver face, a distance between the right end of a driver face and a nose center, and a distance between the left end of a driver face and the nose center in the face direction data.

Such sensing an obstacle includes controlling a direction of the sensing unit that embodies one of a radar, an imaging device (e.g., a camera), a laser, or an ultrasonic sensor to sense an obstacle in a direction (e.g., a second direction) that the driver does not view, and calculating a speed of the vehicle to determine an impact time. Such controlling includes controlling the motor or mechanism operably coupled to the sensing unit so that the sensing unit can be oriented in the second direction.

In embodiments of the present invention, such a method for alarming further includes: outputting an alarm sound (e.g., an auditory signal) so that when there is the obstacle, an alarm is provided to the vehicle such that the vehicle should not enter further into the crossroads/intersections.

In another embodiment, such methods further includes: outputting an alarm sound when there is no obstacle to indicate or alarm such that the vehicle enters in the crossroads/intersection.

In accordance with another aspect of the present invention, there is featured a vehicle using or having such a system for alarming a front impact danger coupled with a driver viewing direction. Such a system includes: a driver viewing direction recognition unit that recognizes a driver viewing direction; an obstacle sensing unit that senses obstacles existing in directions that a driver does not view; and an engine control unit that receives and analyzes driver face direction data from the driver viewing direction recognition unit to identify the driver viewing direction when the vehicle enters in crossroads.

Such an engine control unit also outputs a signal or command to the obstacle sensing unit that requests obstacle sensing for a direction (e.g., a second direction) other than or opposite to the driver viewing direction to the obstacle sensing unit and which analyzes an obstacle sensing result.

In embodiments of the present invention, such a vehicle using system further includes: a navigation unit that provides information regarding the crossroads/intersection and moving direction information of the vehicle to the engine control unit.

The engine control unit checks whether both eyes are detected from the face direction data, calculates a both eyes based direction angle when the both eyes are detected, and calculates a face direction angle when the both eyes are detected or one eye is detected.

The obstacle sensing unit is one of a number of sensing devices as is known to those skilled in the art including but not limited to a device or sensor embodying radar, an imaging device such as a camera, a device or sensor embodying a laser, or an ultrasonic sensor. In further embodiments, a direction of the obstacle sensing unit is changeable such as for, example, by a motor (e.g., indexing electric motor) that is operably coupled to the obstacle sensing unit.

As described above, the present invention advantageously warns a driver as to the presence of obstacles when a vehicle enters in crossroads or an intersection to prevent traffic accident due to a user's carelessness or the carelessness of pedestrian's, joggers or others.

BRIEF DESCRIPTION OF THE DRAWINGS

For a fuller understanding of the nature of the present invention as well as the above and other features of the present invention, reference is made to the following detailed description taken in conjunction with the accompanying drawing figures. In the figures, reference numbers refer to the same or equivalent parts of the present invention throughout the several figures of the drawing.

DETAILED DESCRIPTION

Herein reference shall be made in detail to various exemplary embodiments of the present invention, examples of which are illustrated in the accompanying drawings and described below. The same reference numbers are used throughout the drawings to refer to the same or like parts. Detailed descriptions of well-known functions and structures incorporated herein may be omitted to avoid obscuring the subject matter of the present invention.

A system 90 (FIG. 2) for alarming a front impact danger coupled with a driver viewing direction according to the present invention is described below with reference to FIG. 1 to FIG. 7.

Figure 1:
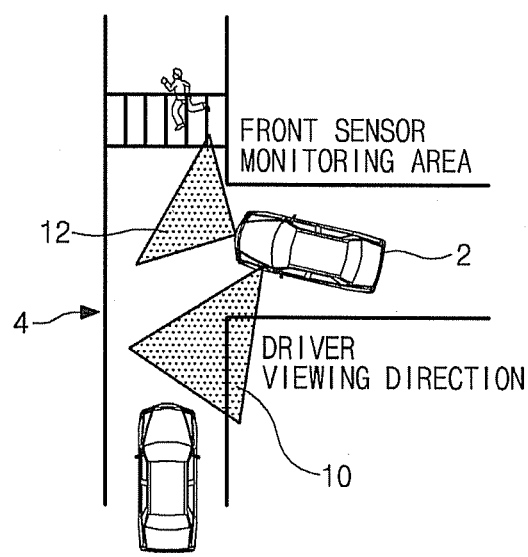
FIG. 1 is an illustrative view of an exemplary crossroads for illustrating vehicle movement and systems and methods of the present invention.

Referring now to FIG. 1, there is shown an illustrative illustrating embodiments of the present invention and movement of a vehicle 2 in the crossroads 4. While a driver is viewing in a direction, a first direction 10, that is opposite to a moving direction of a vehicle to identify oncoming vehicular traffic, the system 90 for alarming a front impact danger coupled with a driver viewing direction senses the moving direction of a vehicle, namely, a front obstacle in another direction, a second direction 12. When there is the front obstacle, the system generates an alarm signal.

Figure 2:
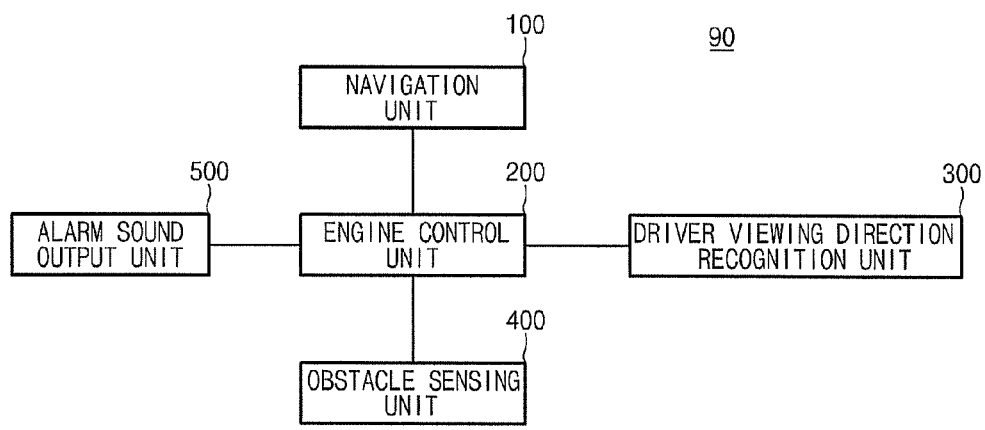
FIG. 2 is a block diagram illustrating a configuration of a system for alarming a front impact danger according to the present invention.

To do this, the system 90 for alarming a front impact danger coupled with a driver viewing direction according to an embodiment of the present invention has a construction as shown in FIG. 2.

Referring now to FIG. 2, there is shown the system 90 for alarming a front impact danger coupled with a driver viewing direction according to the present invention. Such a system includes a navigation unit 100, an engine control unit 200, a driver viewing direction recognition unit 300, an obstacle sensing unit 400, and an alarm sound output unit 500.

When a driver registers a destination, the navigation unit 100 guides a road to the destination for the driver, and transmits crossroads information and user's moving direction information to the engine control unit 200 when a vehicle reaches a crossroads 4.

When the engine control unit 200 receives the crossroads information and the user's moving direction information, it outputs a signal requesting driver viewing direction data from the driver viewing direction recognition unit 300. Accordingly, when the engine control unit 200 receives the driver viewing direction data from the driver viewing direction recognition unit 300, the engine control unit 200 analyzes the driver viewing direction and outputs a signal requesting the obstacle sensing unit 400 to sense for the presence of obstacles in the second direction 12 (direction that a driver does not view) opposite to the driver viewing direction (e.g., to check whether there are obstacles in a direction opposite to the driver viewing direction). When the engine control unit 200 receives an obstacle sensing result from the obstacle sensing unit 400, the engine control unit determines if the vehicle 2 can enter in the crossroads 4 in consideration of the presence of an obstacle in an entry direction of the vehicle and speed of another vehicle coming from a direction opposite to the entry direction of a vehicle. When it is determined that the vehicle 2 should not enter the crossroads 4, the engine control unit 200 generates an alarm sound. In this case, the engine control unit 200 can control generation of the alarm sound only when the vehicle can enter in the crossroads.

The driver viewing direction recognition unit 300 includes an imaging device such as a camera (e.g., a CCD type of camera. When the driver viewing direction recognition unit 300 receives a driver viewing direction recognition request from the engine control unit 200, the driver viewing direction recognition unit images the driver's face and transmits the image data of the driver's face to the engine control unit 200. For example, in the case where the imaging device is a camera, the driver viewing direction recognition unit 300 photographs the driver's face and transmits the photographic data to the engine control unit 200.

When the obstacle sensing unit 400 receives an obstacle sensing request for a specific direction from the engine control unit 200, it performs sensing using one of a radar, a laser, an imaging device (e.g., camera), a laser, or an ultrasonic sensor. The obstacle sensing unit 400 also transmits a sensing result to the engine control unit 200. In further embodiments, the obstacle sensing unit 400 includes a sensing unit or device that embodies one of radar, laser, ultrasonic sensor, or an imaging device (e.g., camera).

In yet further embodiments, the sensing device or sensing unit is controlled by a monitor such that the radar, the laser, the ultrasonic sensor, or imaging device sense an obstacle in a direction (e.g., second direction) not being viewed by the driver and opposite to a driver viewing direction.

When the alarm output unit 500 receives an alarm output signal or request from the engine control unit 200, the alarm output unit outputs an alarm sound (e.g., an auditory signal) so that the driver is informed of the impact danger.

Figure 3:
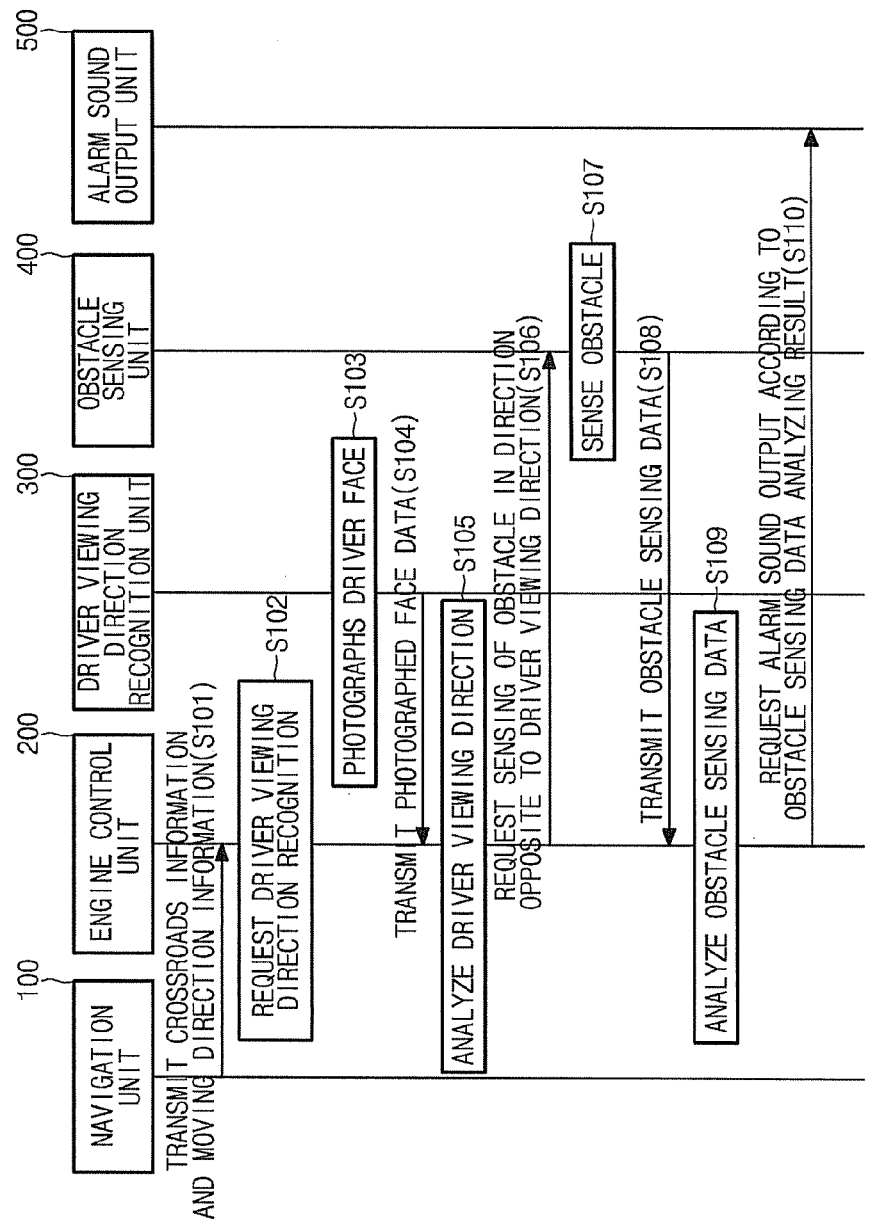
FIG. 3 is a schematic diagram illustrating a method for alarming a front impact danger according to the present invention.
Figure 4:
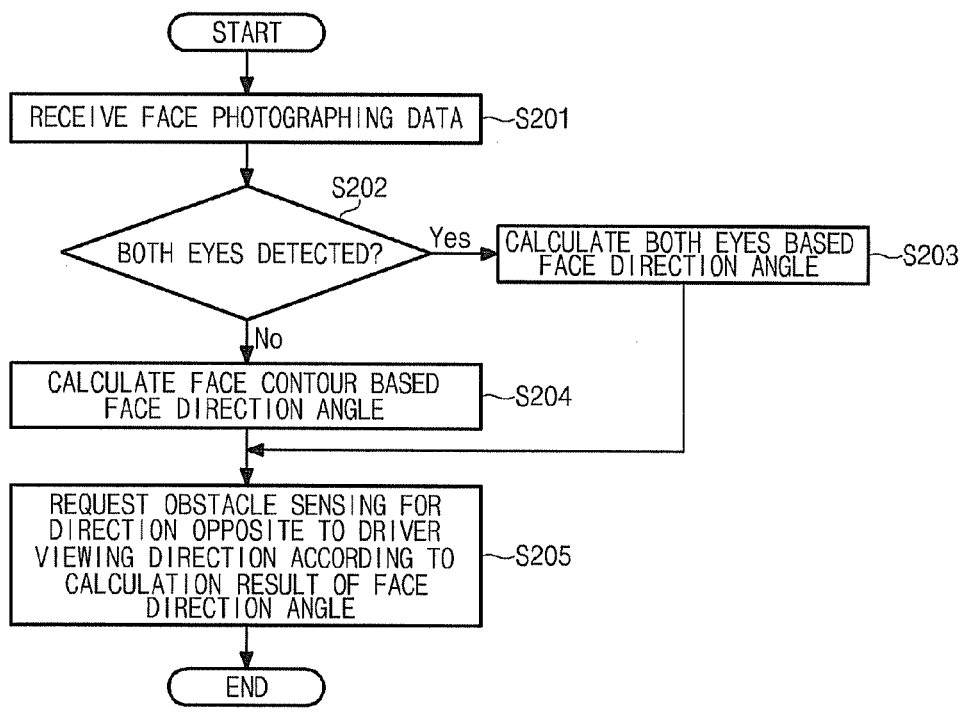
FIG. 4 is a flowchart illustrating a method for analyzing a driver viewing direction of FIG. 3.

Hereinafter, a method for alarming of the potential for a front impact danger coupled with a driver viewing direction according to the present invention is described with particular reference to FIG. 3.

When the engine control unit 200 receives crossroads information and moving direction information from a navigation unit (S101), the engine control unit requests the driver viewing direction recognition unit 300 to perform driver viewing direction recognition (S102). Accordingly, the driver viewing direction recognition unit 300 images (e.g., photographs) the driver's face (S103) and transmits the image data or the photographed data to the engine control unit 200 (S104).

The engine control unit 200 then analyzes the driver face direction and sends a request to the driver viewing direction recognition unit 300 for sensing of obstacles in a direction, a second direction (direction that a driver does not view) or a direction that is opposite to the driver viewing direction. Such sensing is performed by the obstacle sensing unit 400 to check whether obstacles exist in the direction opposite to the driver viewing direction (S106).

Accordingly, the obstacle sensing unit 400 senses obstacles in the second direction or a direction opposite to the driver viewing direction (S107), and transmits obstacle sensing data to the engine control unit 200 (S108). In this case, the obstacle sensing unit 400 senses the obstacle using radar, image data, a laser, or a ultrasonic sensor to sense speed and a moving distance of the obstacle.

Subsequently, the engine control unit 200 analyzes the obstacle sensing data received from the obstacle sensing unit 400 to determine whether there are obstacles (S109). At this time, the engine control unit 200 determines whether a vehicle or other obstacle may enter in a moving direction of the vehicle using speed and moving distance information of the obstacle received from the obstacle sensing unit 400.

In particular, when the driver views moving direction of the vehicle and senses obstacles in a direction opposite to the moving direction of the vehicle, namely, when another vehicle comes from the opposite direction, it is preferable that the engine control unit 200 also calculates an impact time according to speed of the vehicle and guides the vehicle 2 in the moving direction avoiding the calculated impact time.

Subsequently, the engine control unit 200 causes an alarm sound output to occur according to the obstacle sensing data analyzing result (S110). That is, when there is the obstacle in the vehicle moving direction or the direction opposite to a driver viewing direction, the engine control unit 200 outputs an alarm sound, auditory signal and/or visual signal to the driver representing a warning not to enter the crossroads 4, thereby preventing accident. In the case where it is determined that there is no obstacle in the moving direction or the direction opposite to the driver viewing direction, the engine control unit 200 can generate another alarm sound or generate an auditory signal using the alarm sound output unit 500 as an advisory that the vehicle 2 can enter the crossroads 4.

Referring now to FIGS. 4-7, there is described below a method for analyzing a driver viewing direction shown in FIG. 3 and with reference also to equations (1) and (2).

Figure 5:
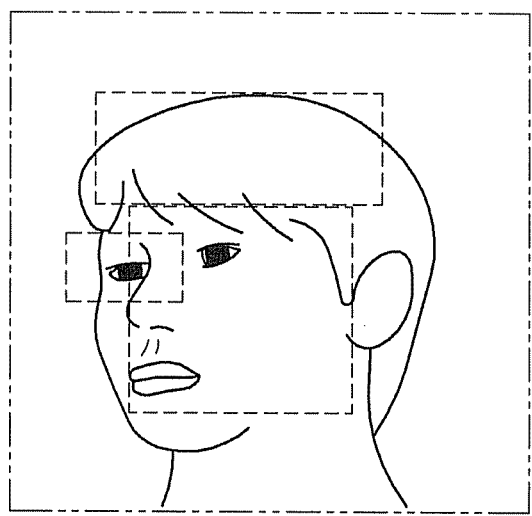
FIG. 5 is an illustrative view illustrating face photographing data of a driver viewing direction recognition unit shown in FIG. 2.

When the engine control unit 200 receives face photographing data or image data as shown in FIG. 5 from the driver viewing direction recognition unit 300 (S201), the engine control unit checks to see if both eyes of the driver are detected (S202).

When the driver's both eyes are detected from the image data/face photographing data, the engine control unit 200 calculates a both eyes based face direction angle using the following equation (1) (S203).

$$\angle NMV = \frac{\overrightarrow{NM} \cdot \overrightarrow{MV}}{\|\overrightarrow{NM}\| \|\overrightarrow{MV}\|} \quad \text{equation (1)}$$

Figure 6:
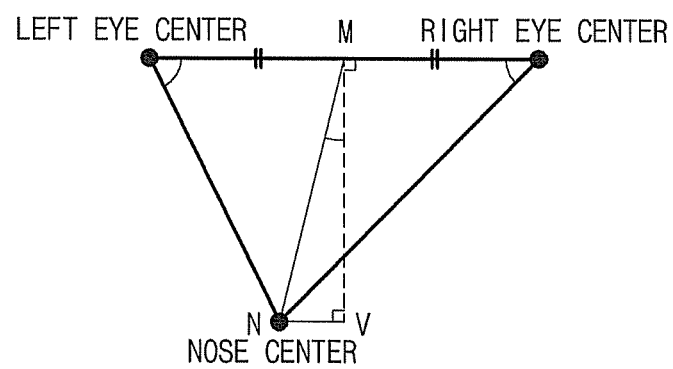
FIG. 6 is an illustrative view illustrating a procedure of calculating a both eyes based face direction angle using the face photographing data of FIG. 5.

Referring to FIG. 6, A triangle, is formed based on center of a left eye, a center of a right eye, and a nose center (N). After a center point(M) of the center of a left eye and the center of a right eye is connected to the nose center (M). An end point(V) of a perpendicular line drawn from the center point M of the center of a left eye and the center of a right eye is connected to the center point(M), A right triangle is formed based on three point(N, M, V). Thus, <NMV of the right triangle is the both eyes based face direction angle.

In this case, when a point V drawing a perpendicular line perpendicular to a line that connects the left eye center and the right eye center from a center point M of the center of a left eye and the center of a right eye is connected to the nose center N to form an right triangle, the angle NMV (<NMV) of the right triangle becomes a both eyes based face direction angle. In particular embodiments, the both eyes based face direction angle, <NMV, is calculated using equation 1.

In the case where both of the driver's eyes are not detected or the driver's eye is detected from the image data/face photographing data, the engine control unit 200 calculates a face direction angle using equation 2 (S204).

$$\text{Face\_Angle}(RL) = \sin^{-1}\left(2 \times \frac{N_X - FR_X}{FL_X - FR_X} - 1\right)[\text{degree}] \quad (2)$$

Figure 7:
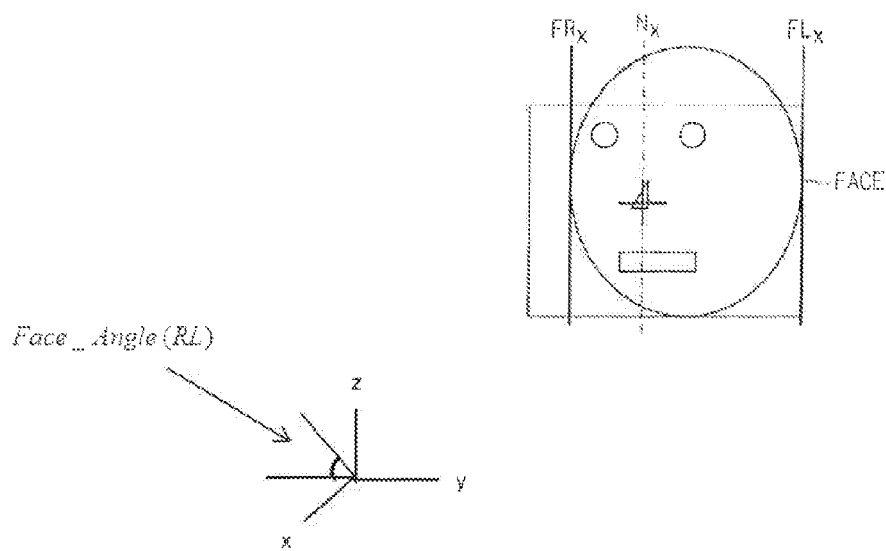
FIG. 7 is an illustrative view illustrating a procedure of calculating a face contour based face direction angle using face photographing data of FIG. 5.

Referring now to FIG. 7, FRx indicates an X axis based right face end, Flx indicates an X axis based left face end, and Nx indicates an X axis based on nose center. Accordingly, the engine control unit 200 calculates a face direction angle Face_Angle (RL) according to the nose center Nx between the right face end FRx and the based left face end FLx. That is, a first value Nx-fRx divided by a second value FL,x-FRx is a third value. The third value multiplied by 2 is a fourth value. 1 subtracted by the fourth value is a fifth value. A reverse sine function for the fifth value is performed to obtain a face direction angle Face_Angle (RL). In this case, the first value Nx-FRx is obtained by subtracting the right face end FRx from the nose center Nx and the second value FLx-FRx is obtained by subtracting the right face end FRx from the left face end FLx.

In this case, the present invention describes an embodiment of calculating a face contour direction angle Face_Angle(RL) through the equation (2). However, the present invention previously calculates the face contour direction angle Face_Angle(RL) by right face ends FRx, left face ends FLx, and nose centers Nx, and stores them in a look-up table form such that they can be used if necessary. Namely, because the face contour direction angle Face_Angle(RL) is stored by right face ends FRx, left face ends FLx, and nose centers Nx, it can be identified without calculation every time.

As indicated herein, the present invention receives crossroads information from the navigation unit and recognizes a driver viewing direction (left/right) when a vehicle enters in crossroads. The present invention checks whether an obstacle(s) exists in a direction, a second direction (i.e., a direction that a driver does not view) or opposite to a drive-viewing direction. When there is no obstacle or although there is an obstacle, the present invention can cause the vehicle 2 to enter a non-impact time, thereby reducing accident generation rate in the crossroads 4.

Although embodiments of the present invention have been described in detail hereinabove, it should be clearly understood that many variations and modifications of the basic inventive concepts herein taught which may appear to those skilled in the present art will still fall within the spirit and scope of the present invention, as defined in the appended claims.

What is claimed is:

1. A system for alarming a front impact danger coupled with a driver viewing direction, comprising:
    an imaging device that recognizes a driver viewing direction;
    a sensing device that senses obstacles existing in directions that a driver does not view; and
    an engine control unit that receives and analyzes driver face direction data from the imaging device to identify the driver viewing direction when the vehicle enters in crossroads, and that request the sensing device to perform obstacle sensing for a direction opposite to the driver viewing direction and to analyze an obstacle sensing result,
    wherein when both eyes are detected from the face direction data, the engine control unit forms a right triangle by connecting a nose center to a center point of a left eye center and a right eye center and connecting a point drawing a line perpendicular to a line that connects the left eye center and the right eye center from the center point of the left eye center and the right eye center to the nose center and calculates an angle toward the center point of the left eye center and the right eye center on the right triangle as the both eyes based face direction angle.

2. The system of claim 1, further comprising a navigation unit that provides information regarding the crossroads and moving direction information of the vehicle to the engine control unit.

3. The system of claim 1, further comprising an alarm sound output unit that outputs an alarm sound responsive to control signals from the engine control unit.

4. The system of claim 1 wherein when the both eyes are not detected or only one eye is detected from the face direction and the engine control unit calculates a face direction angle.

5. The system of claim, 4, wherein the engine control unit calculates the face direction angle using a distance between a right end of a driver face and a left end of the driver face, a distance between the right end of the driver face and a nose center, and a distance between the left end of the driver face and the nose center, in the face direction data.

6. The system of claim 5, wherein the engine control unit calculates the face direction angle using a distance between a right end of a driver face and a left end of the driver face, a distance between the right end of a driver face and a nose center, and a distance between the left end of a driver face and the nose center in the face direction data and stores the calculated face direction angle in a look-up table, and determines a driver viewing direction using the look up table when receiving the face data from the imaging device.

7. The system of claim 1, wherein the sensing device changes a direction of the sensing device by a motor coupled with the imaging device.

8. A method for alarming a front impact danger coupled with a driver viewing direction, comprising:
 receiving, by an engine control unit, crossroads information and moving direction information of a vehicle when the vehicle enters in crossroads;
 checking, by the engine control unit, the driver viewing direction;
 sensing, by the engine control unit, obstacles existing in another direction that the driver does not view using a sensing device; and
 checking, by the engine control unit, if the vehicle enters in the moving direction of the vehicle according to presence of the obstacle as the sensing result of the obstacle,
 wherein when both eyes are detected from the face direction data, the checking the driver viewing direction includes:
  forming a right triangle by connecting a nose center to a center point of a left eye center and a right eye center and connecting a point drawing a line perpendicular to a line that connects the left eye center and the right eye center from the center point of the left eye center and the right eye center to the nose center; and
  calculating an angle toward the center point of the left eye center and the right eye center on the right triangle as the both eyes based face direction angle.

9. The method of claim 8, wherein checking the driver viewing direction comprises:
 imaging, by the engine control unit, a driver face;
 checking, by the engine control unit, whether both eyes are detected from the image data of the driver face; and
 calculating, by the engine control unit, a face direction angle when the both eyes are not detected or one of the both eyes is detected.

10. The method of claim 9, wherein calculating a face direction angle includes calculating, by the engine control unit, the face direction angle using a distance between a right end of a driver face and a left end of the driver face, a distance between the right end of a driver face and a nose center, and a distance between the left end of a driver face and the nose center in the face direction data.

11. The method of claim 8, wherein sensing an obstacle includes controlling a direction of the sensing device embodying one of a radar, an imaging device, a laser, or an ultrasonic sensor, said controlling includes controlling a motor coupled to the sensing device to sense an obstacle in a direction that the driver does not view, and to calculate a speed of the vehicle to determine an impact time.

12. The method of claim 8, further comprising outputting, by the engine control unit, an alarm sound when there is the obstacle to alarm the vehicle so the vehicle does not enter in the crossroads.

13. The method of claim 8, further comprising outputting, by the engine control unit, an alarm sound when there is no obstacle to alarm the vehicle so the vehicle enters in the crossroads.

14. A vehicle using system for alarming a front impact danger coupled with a driver viewing direction, comprising:
 an imaging device that recognizes a driver viewing direction;
 a sensing device that senses obstacles existing in directions that a driver does not view; and
 an engine control unit that receives and analyzes driver face direction data from the imaging device to identify the driver viewing direction when the vehicle enters in crossroads, and that requests obstacle sensing for a direction opposite to the driver viewing direction to the sensing device to analyze an obstacle sensing result,
 wherein when both eyes are detected from the face direction data, the engine control unit forms a right triangle by connecting a nose center to a center point of a left eye center and a right eye center and connecting a point drawing a line perpendicular to a line that connects the left eye center and the right eye center from the center point of the eye center and the right eye center to the nose center and calculates an angle toward the center point of the left eye center and the right eye center on the right triangle as the both eyes based face direction angle.

15. The vehicle of claim 14, further comprising a navigation unit that provides information regarding the crossroads and moving direction information of the vehicle.

16. The vehicle of claim 14, wherein the engine control unit checks whether both eyes are detected from the face direction data and calculates a face direction angle when the both eyes are detected or one eye is detected.

17. The vehicle of claim 14, wherein the sensing device is one of a radar, a camera, a laser, or an ultrasonic sensor.

\* \* \* \* \*